(12) United States Patent
Fontanez et al.

(10) Patent No.: US 11,773,452 B2
(45) Date of Patent: *Oct. 3, 2023

(54) SINGLE CELL SEQUENCING

(71) Applicant: Fluent Biosciences Inc., Watertown, MA (US)

(72) Inventors: Kristina Fontanez, Arlington, MA (US); Robert Meltzer, Belmont, MA (US); Yi Xue, Shrewsbury, MA (US); Sepehr Kiani, Watertown, MA (US)

(73) Assignee: Fluent Biosciences Inc., Watertown, MA (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/407,945

(22) Filed: Aug. 20, 2021

(65) Prior Publication Data

US 2021/0381064 A1 Dec. 9, 2021

Related U.S. Application Data

(63) Continuation of application No. 17/146,986, filed on Jan. 12, 2021, now Pat. No. 11,104,961.

(Continued)

(51) Int. Cl.
  *C12P 19/34* (2006.01)
  *C12Q 1/6886* (2018.01)
  *C12Q 1/686* (2018.01)

(52) U.S. Cl.
  CPC ........... *C12Q 1/6886* (2013.01); *C12Q 1/686* (2013.01); *C12Q 2600/156* (2013.01)

(58) Field of Classification Search
  CPC .................................................. C12Q 1/6869
  See application file for complete search history.

(56) References Cited

U.S. PATENT DOCUMENTS

| | | | |
|---|---|---|---|
| 4,701,415 A | 10/1987 | Dutton | |
| 5,512,439 A | 4/1996 | Hornes et al. | |

(Continued)

FOREIGN PATENT DOCUMENTS

| | | | |
|---|---|---|---|
| AU | 2013203624 A1 | 5/2013 | |
| EP | 3819637 A1 | 5/2021 | |

(Continued)

OTHER PUBLICATIONS

Bowman, 2013, Multiplexed Illumina sequencing libraries from picogram quantities of DNA, BMC Genomics 14:466 (8 pages).

(Continued)

*Primary Examiner* — Kenneth R Horlick
(74) *Attorney, Agent, or Firm* — Withers Bergman LLP; Thomas C. Meyers (57) ABSTRACT

The disclosure provides methods and systems of analyzing single cells by simultaneously separating cells into monodisperse droplets and tagging each nucleic acid molecule from the cells with barcodes unique to each droplet. The methods and systems combine template particles with a plurality of single cells in a tube, generate in the tube monodispersed droplets encapsulating a single one of the template particles and a single one of the single cells, release nucleic acid molecules from the single cells and provide each nucleic acid molecule with a barcode unique to the respective droplet. The nucleic acid molecules can then be analyzed by any known method, for example by sequencing the nucleic acid molecules.

18 Claims, 7 Drawing Sheets

Related U.S. Application Data (60) Provisional application No. 62/960,454, filed on Jan. 13, 2020.

(56) References Cited

U.S. PATENT DOCUMENTS

| | | |
|---|---|---|
| 5,813,759 A | 9/1998 | Gebrian |
| 6,210,891 B1 | 4/2001 | Nyren et al. |
| 6,306,597 B1 | 10/2001 | Macevicz |
| 6,309,833 B1 | 10/2001 | Edman et al. |
| 6,828,100 B1 | 12/2004 | Ronaghi |
| 6,833,246 B2 | 12/2004 | Balasubramanian |
| 6,911,345 B2 | 6/2005 | Quake et al. |
| 7,232,656 B2 | 6/2007 | Balasubramanian et al. |
| 7,537,897 B2 | 5/2009 | Brenner et al. |
| 7,598,035 B2 | 10/2009 | Macevicz |
| 7,835,871 B2 | 11/2010 | Kain et al. |
| 7,842,457 B2 | 11/2010 | Berka et al. |
| 7,960,120 B2 | 6/2011 | Rigatti et al. |
| 8,012,690 B2 | 9/2011 | Berka et al. |
| 8,629,323 B2 | 1/2014 | Weeks |
| 8,715,934 B2 | 5/2014 | Diehl et al. |
| 8,748,102 B2 | 6/2014 | Berka et al. |
| 8,765,380 B2 | 7/2014 | Berka et al. |
| 9,011,777 B2 | 4/2015 | Beer |
| 9,012,390 B2 | 4/2015 | Holtze et al. |
| 9,085,798 B2 | 7/2015 | Chee |
| 9,260,751 B2 | 2/2016 | Diehl et al. |
| 9,388,465 B2 | 7/2016 | Hindson et al. |
| 9,399,797 B2 | 7/2016 | Hutchison et al. |
| 9,562,837 B2 | 2/2017 | Link |
| 9,567,645 B2 | 2/2017 | Fan et al. |
| 9,567,646 B2 | 2/2017 | Fan et al. |
| 9,580,736 B2 | 2/2017 | Tan et al. |
| 9,598,736 B2 | 3/2017 | Fan et al. |
| 9,637,799 B2 | 5/2017 | Fan et al. |
| 9,650,629 B2 | 5/2017 | Froehlich et al. |
| 9,695,474 B2 | 7/2017 | Johnson et al. |
| 9,701,998 B2 | 7/2017 | Hindson et al. |
| 9,708,654 B2 | 7/2017 | Hunicke-Smith et al. |
| 9,783,847 B2 | 10/2017 | Chee |
| 9,951,386 B2 | 4/2018 | Hindson et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,151,003 B2 | 12/2018 | Fan et al. |
| 10,155,981 B2 | 12/2018 | Brenner et al. |
| 10,202,628 B2 | 2/2019 | Church et al. |
| 10,208,356 B1 | 2/2019 | Fan et al. |
| 10,221,442 B2 | 3/2019 | Hindson et al. |
| 10,240,192 B2 | 3/2019 | Berka et al. |
| 10,240,197 B1 | 3/2019 | Brenner et al. |
| 10,253,375 B1 | 4/2019 | Fan et al. |
| 10,266,883 B2 | 4/2019 | Chee |
| 10,280,459 B1 | 5/2019 | Brenner et al. |
| 10,285,940 B2 | 5/2019 | Mason et al. |
| 10,329,557 B2 | 6/2019 | Johnson et al. |
| 10,344,329 B2 | 7/2019 | Hindson et al. |
| 10,392,662 B1 | 8/2019 | Brenner et al. |
| 10,400,280 B2 | 9/2019 | Hindson et al. |
| 10,415,030 B2 | 9/2019 | Marshall et al. |
| 10,457,986 B2 | 10/2019 | Hindson et al. |
| 10,501,793 B2 | 12/2019 | Chee |
| 10,584,381 B2 | 3/2020 | Hindson et al. |
| 11,060,149 B2 | 7/2021 | Steelman |
| 11,104,961 B2 | 8/2021 | Fontanez et al. |
| 11,142,791 B2 | 10/2021 | Abate et al. |
| 2002/0132251 A1 | 9/2002 | Shuber |
| 2003/0143599 A1 | 7/2003 | Makarov et al. |
| 2003/0180737 A1 | 9/2003 | Gu et al. |
| 2004/0005585 A1 | 1/2004 | Bi et al. |
| 2006/0024681 A1 | 2/2006 | Smith et al. |
| 2006/0177836 A1 | 8/2006 | McKernan et al. |
| 2006/0292611 A1 | 12/2006 | Berka et al. |
| 2007/0080316 A1 | 4/2007 | Sauer et al. |
| 2007/0114362 A1 | 5/2007 | Feng et al. |
| 2008/0004436 A1 | 1/2008 | Tawfik |
| 2009/0280475 A1 | 11/2009 | Pollack et al. |
| 2011/0009278 A1 | 1/2011 | Kain et al. |
| 2011/0086780 A1 | 4/2011 | Colston, Jr. et al. |
| 2011/0118151 A1 | 5/2011 | Eshoo et al. |
| 2011/0311978 A1 | 12/2011 | Makarewicz, Jr. et al. |
| 2012/0295269 A1 | 11/2012 | Pourahmadi et al. |
| 2012/0316074 A1 | 12/2012 | Saxonov |
| 2013/0115169 A1 | 5/2013 | Lahann et al. |
| 2014/0155295 A1 | 6/2014 | Hindson et al. |
| 2015/0133312 A1 | 5/2015 | Bielas et al. |
| 2015/0225777 A1 | 8/2015 | Hindson et al. |
| 2016/0186267 A1 | 6/2016 | So et al. |
| 2016/0250608 A1 | 9/2016 | Anders et al. |
| 2016/0274103 A1 | 9/2016 | Piloto et al. |
| 2017/0192030 A1 | 7/2017 | Lapham et al. |
| 2017/0218437 A1 | 8/2017 | Seul et al. |
| 2017/0232417 A1 | 8/2017 | Lebofsky et al. |
| 2017/0255160 A1 | 9/2017 | Numata et al. |
| 2018/0010105 A1 | 1/2018 | Rogers et al. |
| 2018/0051321 A1 | 2/2018 | Hindson et al. |
| 2018/0119216 A1 | 5/2018 | Jamshidi et al. |
| 2018/0133715 A1 | 5/2018 | Craig et al. |
| 2018/0179553 A1 | 6/2018 | Watson et al. |
| 2018/0216162 A1 | 8/2018 | Belhocine et al. |
| 2018/0237836 A1 | 8/2018 | Abate et al. |
| 2018/0274027 A1 | 9/2018 | Hindson et al. |
| 2018/0355407 A1 | 12/2018 | Utharala et al. |
| 2019/0085412 A1 | 3/2019 | Fan et al. |
| 2019/0153532 A1 | 5/2019 | Bharadwaj et al. |
| 2019/0153550 A1 | 5/2019 | Steinmetzer et al. |
| 2019/0177789 A1 | 6/2019 | Hindson et al. |
| 2019/0323003 A1 | 10/2019 | Ramji et al. |
| 2019/0323091 A1 | 10/2019 | Bramlett et al. |
| 2019/0352714 A1 | 11/2019 | Salk et al. |
| 2019/0381497 A1 | 12/2019 | Di Carlo et al. |
| 2019/0382753 A1 | 12/2019 | Steemers et al. |
| 2020/0040385 A1 | 2/2020 | Beechem et al. |
| 2020/0080112 A1 | 3/2020 | Zhang et al. |
| 2020/0190513 A1 | 6/2020 | Fernandez et al. |
| 2020/0261879 A1 | 8/2020 | Abate et al. |
| 2020/0324287 A1 | 10/2020 | Vijayan et al. |
| 2020/0376488 A1 | 12/2020 | Wu et al. |
| 2021/0010070 A1 | 1/2021 | Schnall-Levin et al. |
| 2021/0054369 A1 | 2/2021 | Meltzer et al. |
| 2021/0214721 A1 | 7/2021 | Fontanez et al. |
| 2021/0214763 A1 | 7/2021 | Fontanez et al. |
| 2021/0214769 A1 | 7/2021 | Fontanez et al. |
| 2021/0214792 A1 | 7/2021 | Fontanez et al. |
| 2021/0214802 A1 | 7/2021 | Fontanez et al. |
| 2021/0215591 A1 | 7/2021 | Fontanez et al. |
| 2021/0301354 A1 | 9/2021 | Kiani et al. |
| 2021/0332432 A1 | 10/2021 | Kiani et al. |
| 2021/0340596 A1 | 11/2021 | Meltzer et al. |
| 2021/0381064 A1 | 12/2021 | Fontanez et al. |
| 2022/0017892 A1 | 1/2022 | Meltzer et al. |
| 2022/0135966 A1 | 5/2022 | Meltzer |
| 2022/0136071 A1 | 5/2022 | Meltzer |
| 2022/0154248 A1 | 5/2022 | Abate et al. |
| 2022/0235416 A1 | 7/2022 | Fontanez et al. |
| 2022/0267761 A1 | 8/2022 | Fontanez et al. |

FOREIGN PATENT DOCUMENTS

| | | |
|---|---|---|
| JP | 2021072863 A | 5/2021 |
| WO | 1997/008547 A1 | 3/1997 |
| WO | 2010/117620 A2 | 10/2010 |
| WO | 2011/047307 A1 | 4/2011 |
| WO | 2012/116146 A1 | 8/2012 |
| WO | 2012/149042 A2 | 11/2012 |
| WO | 2013/165748 A1 | 11/2013 |
| WO | 2014/028537 A1 | 2/2014 |
| WO | 2014/100434 A1 | 6/2014 |
| WO | 2014/146025 A1 | 9/2014 |
| WO | 2014/153071 A1 | 9/2014 |
| WO | 2015/157369 A1 | 10/2015 |
| WO | 2015/187792 A1 | 12/2015 |
| WO | 2016/025815 A1 | 2/2016 |
| WO | 2016/040476 A1 | 3/2016 |

(56) References Cited

FOREIGN PATENT DOCUMENTS

| WO | 2016/126871 A2 | 8/2016 |
|---|---|---|
| WO | 2016/138080 A1 | 9/2016 |
| WO | 2016/172373 A1 | 10/2016 |
| WO | 2017/161306 A1 | 9/2017 |
| WO | 2019/011971 A1 | 1/2019 |
| WO | 2019/023627 A1 | 1/2019 |
| WO | 2019/139650 A2 | 7/2019 |
| WO | 2019/157529 A1 | 8/2019 |
| WO | 2019/204229 A1 | 10/2019 |
| WO | 2019/217552 A1 | 11/2019 |
| WO | 2019/222523 A2 | 11/2019 |
| WO | 20200037214 A1 | 2/2020 |
| WO | 2020/069268 A1 | 4/2020 |
| WO | 2020/069298 A1 | 4/2020 |

OTHER PUBLICATIONS

Eastburn, 2013, Ultrahigh-trhoughput mammalian single-cell reverse-transcriptase polymerase chain reaction in microfluidic drops, Anal Chem 85:8016-8021.
Figueiredo, 2007, Cost effective method for construction of high quality cDNA libraries, Biomol Eng 24:419-421.
Fu, 2015, Uniform and accurate single-cell sequencing based on emulsion whole-genome amplification, PNAS 112(38):11923-11928.
Hatori, 2019, Particle-Templated Emulsification for Microfluidics-Free Digital Biology, Analytical Chemistry, 90:9813-9820.
Int Search Report and Written Op dated Apr. 1, 2021, for Int Application No. PCT/US2021/013069, filed Jan. 12, 2021 (14 pages).
Int Search Report and Written Op dated Aug. 11, 2021, for Int Application No. PCT/US2021/022503, filed Mar. 16, 2021 (9 pages).
Int Search Report and Written Op dated Feb. 2, 2021, for Int Application No. PCT/US2020/47214, filed Aug. 20, 2020 (14 pages).
Int Search Report and Written Op dated Jun. 30, 2021, for Int Application No. PCT/US2021/023815, filed Mar. 24, 2021 (14 pages).
Int Search Report and Written Op dated Mar. 29, 2021, for Int Application No. PCT/US2021/013042, filed Jan. 12, 2021 (9 pages).
Int Search Report and Written Op dated Mar. 29, 2021, for Int Application No. PCT/US2021/013045, filed Jan. 12, 2021 (8 pages).
Int Search Report and Written Op dated Mar. 29, 2021, for Int Application No. PCT/US2021/013065, filed Jan. 12, 2021 (11 pages).
Int Search Report and Written Op dated Mar. 29, 2021, for Int Application No. PCT/US2021/013066, filed Jan. 12, 2021 (11 pages).
Int Search Report and Written Op dated Mar. 31, 2021, for Int Application No. PCT/US2021/013048, filed Jan. 12, 2021 (20 pages).
Kumaresan, 2008, High-throughput single copy DNA amplification and cell analysis in engineered nanoliter droplets, Anal Chem, 80:3522-3529.
Kumari, 2017, Quantification of Circulating Free DNA as a Diagnostic Marker in Gall Bladder Cancer, Pathology & Oncology Research, 23:91-97.
Lage, 2003, Whole genome analysis of genetic alterations in small DNA samples using hyperbranched strand displacement amplification and array-CGH, Genome Res 13:294-307.
Lyons, 2017, Large-scale DNA barcode library generation for biomolecule identification in high-throughput screens, Sci Rep 7:13899 (7 pages).
Mazutis, 2013, Singl-cell analysis and sorting using droplet-based microfluidics, Nature Protocols, 8(5):870-891.
Nishikawa, 2015, Monodisperse picoliter droplets for low-bias and contamination-free reactions in single-cell whole genome amplification, PLoSOne 10(9):e0138733 (15 pages).
Roche, 2011, emPCR amplificaiotn method manual, 454 Life Sciences Corp (12 pages).
Sidore, 2016, Enhanced sequencing coverage with digital droplet multiple displacement amplification, Nucl Acids Res 44(7):e66 (9 pages).
Stoeckius, 2017, Simultaneous epitope and transcriptome measurment in single cells, Nat Meth online pub (10 pages).
Tamminen, 2015, Single gene-based distinction of individual microbial genomes from a mixed population of microbial cells Front Microb 6:195 (10 pages).
Vitale, 2019, An Optimized Workflow to Evaluate Estrogen Receptor Gene Mutations in Small Amounts of Cell-Fee DNA, The Journal of Molecular Diagnostics, 21(1):123-127.
Walls, 2020, Structure, Function, and Antigenicity of the SARS-CoV-2 Spike Glcoprotein, Cell, 181(2):281-292.
Zilionis, 2016, Single-cell barcoding and sequencing using droplet microfluidics, Natutre Prot 12(1):44-73.
Berensmeier, 2006, Magnetic particles for the separation and purification of necleic acids, Applied Microbiology and Biotechnology, 73:495-504.
Biocompare, 2013, Howto maintain a constant temp in your CO2 incubator, Jan. 17, 2013 (Jan. 17, 2013) [online] retrieved from <URL: https://www.biocompare.com/Editorial-Articles/126328-Incubators/#:~text=A jacket of water circulates, thermal buffer against outside air.> entire document, 7 pages.
Brouzes, 2009, Droplet microfluidic technology for single-cell high-throughput screening, Proc Natl Acad Sci 106(34):14195-14200.
Cai, 2019, Selection of DNA-encoded libraries to protein targets within and on living cells, Journal of the American Chemical Society, 141(43):1-11.
Cheng, 2020, Ultra-senstive and rapid detection of nucleic acids and microorganisms in body fluids using single molecule tethering, Nature Communications, 11(1):1-9.
Datlinger, 2017, Pooled CRISPR screening with single-cell transcriptome readout, Nature Methods 4(3):297-301.
High containment laboratories at CDC—Fifty Years of Excellence, Centers for Disease Control and Prevention, retreived from the internet, <https://www.cdc.gov/ncezid/dhcpp/hcl-50/high-containment-laboratories.html>, 1 page, (2019).
Jacobsen, 2004, Direct isolation of poly(A)+ RNA from 4 M guanidine thiocyanate-lysed cell extracts using locked nucleic acid-oligo(T) capture, Nucleic Acids Research, 32(7), 10 pages.
Kim, 2018, Single-Cell RT-PCR in Microfluidic Droplets with Integrated Chemical Lysis, Anal Chem 90(2):1273-1279.
Klein, 2015, Droplet barcoding for single cell transcriptomics applied to embryonic stem cells, Cells, 161(5):1187-1201.
Kukurba, 2015, RNA Sequencing and Analysis, Cold Spring Harb Protoc 11:951-969.
Markus, 2021, Analysis of recurrently protected genomic regions in cell-free DNA found in urine, Science Translational Medicine, 13(581):1-31.
Patel, 2019, Design and fabrication of low cost vortex mixer using additive manufacturing, International Journal of Applied Engineering Research 14(1):246-249.
Petersen, 2021, Screening of DNA-encoded small molecule libraries inside a living cell, Journal of the American Chemical Society, 143(7):2751-2756.
Quail, 2012, A tale of three next generation sequencing platforms: comparison of Ion Torrent, Pacific Biosciences and Illumina MiSeq sequencers, BMC Genomics 13:341, 13 pages.
Replogle, 2020, Combinatorial single-cell CRISPR screens by direct guide RNA capture and targeted sequencing, Nat. Biotechnol. 38(8):954-961.
Stoeckius, 2017, Large-scale simultaneous measurements of epitopes and transcriptomes in single cells, Nat Methods 14(9):865-868.
Tokunaga, 2013, Systematic exploration of lipophilic tags that allow efficient anchoring of aptamers to live cell surfaces, Chem Lett 42(2):127-129.

SINGLE CELL SEQUENCING

CROSS-REFERENCE TO RELATED APPLICATION

This application is a continuation of U.S. patent application Ser. No. 17/146,986, filed Jan. 12, 2021, (granted as U.S. Pat. No. 11,104,961), which claims the benefit of, and priority to, U.S. Provisional Patent Application Ser. No. 62/960,454, filed Jan. 13, 2020, the contents of each of which are incorporated by reference.

FIELD OF THE INVENTION

The invention relates to methods and systems for single cell analysis.

BACKGROUND

A major challenge in treating cancer is the difficulty and cost of detecting cancer cells from among healthy cells at an early stage when cancer treatment is most effective. The identification of cells and cellular components that exist in small proportion against a background of a more common cellular material is a significant problem in diagnostics. Numerous solutions to this problem have been proposed. For example, single-cell sequencing has been proposed as a way to identify cancer cells that are present in small proportion in a sample. Traditional methods for isolating single cells employ flow cytometry and droplet microfluidics to separate single cells one at a time. Those methods, however, require complicated equipment that is both expensive and difficult to use. Moreover, because each cell must be processed individually, such methods are rate limited and require extensive periods of time (often days) to separate cancer cells from surrounding cells. That limitation is especially problematic in early cancer detection where the proportion of cancer cells in a sample is at its smallest. Additionally, because such methods are difficult to use, particularly by clinicians, samples must be sent to facilities capable of handling such equipment, further increasing the time and expense needed to reach a cancer diagnosis. This has resulted in early cancer detection being unaffordable and unavailable to the majority of cancer patients.

SUMMARY OF THE INVENTION

The invention provides methods and systems for single cell analysis that greatly reduce the complexity and cost of single cell sequencing and early cancer detection. Methods of the invention separate single cells in a sample simultaneously, rather than one by one, by encapsulating each cell into individual monodispersed droplets together with barcodes unique to each droplet. These barcodes can then be provided to nucleic acid molecules released from each single cell and, once sequenced, the nucleic acid molecules can be traced back to the droplet. Because each droplet encapsulates only a single cell, the nucleic acid molecules thereby provide genotypic information about the cell. By separating cells into droplets simultaneously, rather than individually, and tagging nucleic molecules with barcodes unique to each droplet, these methods allow for the separation of cancer cells from a sample within hours, rather than days, providing for faster and earlier cancer detection. Additionally, methods of the present invention are performed without the need for complex and expensive machinery as required by microfluidic cell separation techniques, dramatically reducing the cost of single cell analysis and early cancer detection.

Moreover, methods of the present invention provide an approach that is easily scalable from small to large volumes of samples and can be automated. By reducing the complexity of single cell analysis, the methods and systems of the present invention allow clinicians themselves to prepare samples for single cell analysis, further reducing the cost of early cancer detection. This dramatic reduction in the cost and time needed for single cell analysis greatly increases the population to whom early cancer detection will be available.

The present invention is achieved, in part, by combining template particles with a plurality of single cells in a tube and generating in the tube a plurality of monodispersed droplets simultaneously that encapsulate a single one of the template particles and a single one of the single cells. Nucleic acids are released from the single cells and each nucleic acid molecule within a droplet is provided with a barcode unique to the droplet. Each nucleic acid molecule may then be analyzed by any known method, for example by sequencing the nucleic acid. The nucleic acid molecule may be any nucleic molecule, including DNA and/or RNA.

Methods of the present invention simultaneously separate single cells by combining the template particles with the single cells in a first fluid, adding a second fluid to the first fluid, and shearing the fluids to generate a plurality of monodispersed droplets simultaneously that contain a single one of the template particles and a single one of the single cells. Methods of releasing nucleic acid molecules from the single cells may further include lysing the single cells within the monodispersed droplets to release nucleic acid molecules that are subsequently tagged with barcodes unique to each droplet such that a nucleic acid molecule originating from any droplet can be identified.

In such methods the first fluid and the second fluid may be immiscible. For example, the first fluid may comprise an aqueous phase fluid and/or the second fluid may comprise an oil. The first fluid may comprise reagents selected from, for example, buffers, salts, lytic enzymes (e.g. proteinase k) and/or other lytic reagents (e. g. Triton X-100, Tween-20, IGEPAL, or combinations thereof), nucleic acid synthesis reagents e.g. nucleic acid amplification reagents or reverse transcription mix, or combinations thereof. The second fluid may comprise fluorocarbon oil, a silicone oil, or a hydrocarbon oil, or a combination thereof. Shearing fluids may comprise vortexing, shaking, flicking, stirring, pipetting, or any known method for mixing solutions.

Droplets generated by methods of the present invention are monodisperse and encapsulate a single one of the template particles and a single one of the single cells. Advantageously, the template particles may each provide a barcode unique to that template particle. Because each droplet only encompasses one template particle and one single cell, by doing so the template particles provides a barcode that is also unique to each droplet and therefore unique to the cell encapsulated in each droplet.

Template particles may comprise any known particles that can be used for forming the monodispersed droplets and advantageously may provide barcodes unique to each droplet. The template particles may be hydrogels, for example, hydrogels comprising agarose, alginate, a polyethylene glycol (PEG), a polyacrylamide (PAA), acrylate, acrylamide/bis-acrylamide copolymer matrix, azide-modified PEG, poly-lysine, polyethyleneimine, and combinations thereof. In certain instances, template particles may be shaped to provide an enhanced affinity for the single cells. For example, the template particles may be generally spherical but the shape may contain features such as flat surfaces, craters, grooves, protrusions, and other irregularities in the spherical shape that promote an association with a single cell such that the shape of the template particle increases the probability of templating a monodisperse droplet that contains a single cell.

Additionally, the template particles may further comprise one or more compartments. For example, the one or more compartments may contain one or more of a lytic reagent, a nucleic acid synthesis reagent, the barcodes unique to each droplet, or a combination thereof. It may be advantageous for the nucleic acid synthesis reagent to comprise a polymerase, for example when PCR is desired. When using a reagent, the reagent may be released from the one or more compartments in response to an external stimulus.

Template particles may also comprise a plurality of capture probes comprising one or more of a primer sequence, the barcode unique to each droplet, a unique molecule identifier (UMI), and/or a capture sequence. The primer sequence may comprise a binding site comprising a sequence that would be expected to hybridize to a complementary sequence, if present, on any nucleic acid molecule released from a cell and provide an initiation site for a reaction, for example an elongation or polymerization reaction. Capture probes comprising the barcode unique to each droplet, the capture probes may be use to tag the nucleic molecules released from single cells with the barcode. Capture sequences may be used in capture probes to target gene-specific nucleotide sequences.

Tubes for single cell analysis of the present invention may be selected based on the volume of sample from which cells need to be separated and/or based on the number of cells to be separated. For example, the tube may be single large tube, such as a conical centrifuge tube, such as a Falcon® as sold by Corning Inc., Corning, N.Y., for example a tube with a volume of less than 40 mL. The tubes may also be wells, such as standard 96 sample well kits. The tubes may also be centrifuge, microcentrifuge, or PCR tubes, such as those sold be Eppendorf®, Hamburg, Germany. Such tubes, for example, may be between 0.1 and 6 mL.

For any tubes sample preparation for sequencing may be completed within one day, and advantageously can be completed within three hours. Moreover, preparation of samples within each tube may be completed in as little time as about 5 minutes or about 2 minutes. This is in contrast to preparation of cells by microfluidics which often require three days for sample preparation, and further advantageous over prior emulsion based preparations which required, at least, additional steps and time for barcoding each nucleic acid molecule.

Methods for sequencing nucleic acid molecules are well known and the present invention may comprise any known method for nucleic acid sequencing, for example Sanger sequencing or next-generation sequencing. In methods of the present invention, sequencing comprises detection of a mutation, such as a cancer mutation. Advantageously, the present invention allows for detection of a mutation where the mutation has a frequency in cells in a sample of less than 0.05%. Accordingly, the present invention allows to detection if cancer cells from small volumes of DNA, for example less 10 ng of DNA. Methods of the present invention are applicable to any known human sample. For example, the above methods are readily applicable to the analysis of a tumor taken from a subject, such as from a tumor biopsy. By nucleic acid sequencing, cancer cells may be identified from the biopsy and the patient may be diagnosed with cancer.

DETAILED DESCRIPTION

The present invention provides methods and systems of analyzing single cells by combining template particles with a plurality of single cells in a tube and generating in the tube a plurality of monodispersed droplets simultaneously that encapsulate a single one of the template particles and a single one of the single cells. Nucleic acids are released from the single cells and each nucleic acid molecule within a droplet is provided with a barcode unique to the droplet. Each nucleic acid molecule may then be analyzed by any known method, for example by sequencing the nucleic acid. The nucleic acid molecule may be any nucleic molecule, including DNA and/or RNA.

The barcodes may be any group of nucleotides or oligonucleotide sequences that are distinguishable from other barcodes within the group. A droplet encapsulating a template particle and a single cell provides to each nucleic acid molecule released from the single cell the same barcode from the group of barcodes. The barcodes provided by each droplet are unique to that droplet and distinguishable from the barcodes provided to nucleic acid molecules by every other droplet. Once sequenced, by using the barcode sequence, the nucleic acid molecules can be traced back to the droplet and thereby to each single cell. Barcodes may be of any suitable length sufficient to distinguish the barcode from other barcodes. For example, a barcode may have a length of 4, 5, 6, 7, 8, 9, 10, 11, 12, 13, 14, 15, 16, 17, 18, 19, 20, 21, 22, 23, 24, 25 nucleotides, or more. The barcodes may be pre-defined, degenerate, and/or selected at random.

Barcodes may be added to nucleic acid molecules by "tagging" the nucleic acid molecules with the barcode. Tagging may be performed using any known method for barcode addition, for example direct ligation of barcodes to one or more of the ends of each nucleic acid molecule. Nucleic acid molecules may, for example, be end repaired in order to allow for direct or blunt-ended ligation of the barcodes. Barcodes may also be added to nucleic acid molecules through first or second strand synthesis, for example using capture probes, as described herein below.

Template particles may comprise any known particles that can be used for forming the monodispersed droplets and advantageously may provide barcodes unique to each droplet. Template particles for single cell analysis leverage the particle-templated emulsification technology previously described in, Hatori et. al., Anal. Chem., 2018 (90):9813-9820, which is incorporated by reference. Most frequently, micron-scale beads (such as hydrogels) may be used to define an isolated fluid volume surrounded by an immiscible partitioning fluid and stabilized by temperature insensitive surfactants.

The template particles of the present disclosure may be prepared using any method known in the art. Generally, the template particles are prepared by combining hydrogel material, e.g., agarose, alginate, a polyethylene glycol (PEG), a polyacrylamide (PAA), Acrylate, Acrylamide/bisacrylamide copolymer matrix, and combinations thereof. Following the formation of the template particles they are sized to the desired diameter for capturing and uniquely tagging cells. For example, sizing of the template particles may be done by microfluidic co-flow into an immiscible oil phase.

Template particles may vary in size. Variation may be limited, for example the diameter or largest dimension of the template particles may be such that at least 50% or more, e.g., 60% or more, 70% or more, 80% or more, 90% or more, 95% or more, or 99% or more of the template particles vary in diameter or largest dimension by less than a factor of 10, e.g., less than a factor of 5, less than a factor of 4, less than a factor of 3, less than a factor of 2, less than a factor of 1.5, less than a factor of 1.4, less than a factor of 1.3, less than a factor of 1.2, less than a factor of 1.1, less than a factor of 1.05, or less than a factor of 1.01.

Advantageously, the absorbency of the presently disclosed template particles may be increased by storing them in a dehydrated condition prior to using them in the presently disclosed method for single cell analysis, with the general intention of shrinking their volume. Advantageously, shrinking template particles allows for control of the template particle shape and size for capturing cells and barcoding released nucleic acid molecule, for example with barcodes unique to each droplet. For example, dehydration of the template particles may be achieved by storing them in a high osmolarity buffer to promote shrinking (i.e. Polyethelene glycol). Alternatively, the template particles may be may be ethanol dehydrated. Shrinking may occur upon the application of an external stimulus, e.g., heat. For instance, advantageously the template particles may be encapsulated in a fluid by shearing, followed by the application of heat, causing the template particles to shrink in size. Some other examples of drying approaches include, but are not limited to, heating, drying under vacuum, freeze drying, and supercritical drying. The dried template particles may also be combined with a fluid, but still retain the shape and structure as independent, often spherical, gel particles. The dried template particles may be combined with an appropriate fluid, causing a portion of the fluid to be absorbed by the template particles. Porosity of the template particles may also vary, to allow at least one of a plurality of cells to be absorbed into the template particles when combined with the appropriate fluid. Any convenient fluid that allows for the desired absorption to be performed in the template particles may be used.

Template particles are advantageously tiny, generally spherical, particles. Template particles may be porous or nonporous. Template particles may also include microcompartments or internal compartments which advantageously may contain additional components and/or reagents, for example, additional components and/or reagents that may be releasable into monodisperse droplets. Advantageously, template particles may include microcompartments which include the barcodes unique to each droplet for use in tagging nucleic acid molecules released from a single cell within the droplet.

Template particles for such use may include a polymer such as a hydrogel. Template particles generally range from about 0.1 to about 1000 µm in diameter or largest dimension. Template particles may have a diameter or largest dimension of about 1.0 µm to 1000 µm, inclusive, such as 1.0 µm to 750 µm, 1.0 µm to 500 µm, 1.0 µm to 250 µm, 1.0 µm to 200 µm, 1.0 µm to 150 µm 1.0 µm to 100 µm, 1.0 µm to 10 µm, or 1.0 µm to 5 µm, inclusive. Template particles may have a diameter or largest dimension of about 10 µm to about 200 µm, e.g., about 10 µm to about 150 µm, about 10 µm to about 125 µm, or about 10 µm to about 100 µm.

Cells analyzed by the present invention may include live cells obtained from, for example, a sample (tissue of bodily fluid) of a patient. The sample may include a fine needle aspirate, a biopsy, or a bodily fluid from the patient. Upon being isolated from the sample, the cells may be processed by, for example, generating a single cell suspension with an appropriate solution. Such solution will generally be a balanced salt solution, e.g. normal saline, PBS, HBSS (Hank's balanced salt solution), etc., and in certain instances supplemented with fetal calf serum or other naturally occurring factors, in conjunction with an acceptable buffer at low concentration, generally from 5-25 mM. Convenient buffers include HEPES, phosphate buffers, lactate buffers, etc. The separated cells can be collected in any appropriate medium that maintains the viability of the cells, usually having a cushion of serum at the bottom of the collection tube. Various media are commercially available and may be used according to the nature of the cells, including dMEM, HBSS, DPBS, RPMI, IMDM (Iscove's medium), etc., frequently supplemented with fetal calf serum. Preferably, the cells are mammal cells, for example human cells.

The composition and nature of the template particles may vary depending on the single cell analysis being conducted. For instance, the template particles may be microgel particles that are micron-scale spheres of gel matrix. The microgels are composed of a hydrophilic polymer that is soluble in water, including alginate or agarose. Microgels may also be composed of a lipophilic microgel.

Template particles may also be a hydrogel, such as hydrogels from naturally derived materials, synthetically derived materials, and combinations thereof. Examples of hydrogels include, but are not limited to, collagen, hyaluronan, chitosan, fibrin, gelatin, alginate, agarose, chondroitin sulfate, polyacrylamide, polyethylene glycol (PEG), polyvinyl alcohol (PVA), acrylamide/bisacrylamide copolymer matrix, polyacrylamide/poly(acrylic acid) (PAA), hydroxyethyl methacrylate (HEMA), poly N-isopropylacrylamide (NIPAM), and polyanhydrides, poly(propylene fumarate) (PPF).

Template particles may further advantageously comprise materials which provide the template particles with a positive surface charge, or an increased positive surface charge. Such materials may be without limitation poly-lysine or Polyethyleneimine, or combinations thereof. This may increase the chances of association between the template particle and, for example, a cell which generally have a mostly negatively charged membrane.

Other strategies aimed to increase the chances of template particle-cell association include creation of a specific template particle geometry. For example, the template particles may have a general spherical shape but the shape may contain features such as flat surfaces, craters, grooves, protrusions, and other irregularities in the spherical shape.

Any one of the above described strategies and methods, or combinations thereof may be used in the practice of the presently disclosed template particles and method for single cell analysis thereof. Methods for generation of template particles, and template particles-based encapsulations, were described in International Patent Publication WO 2019/139650, which is incorporated herein by reference.

Creating template particle-based encapsulations for single cell analysis may comprise combining single cells with a plurality of template particles in a first fluid to provide a mixture in a reaction tube. The mixture may be incubated to allow association of the plurality of the template particles with single cells. A portion of the plurality of template particles may become associated with the single cells. The mixture is then combined with a second fluid which is immiscible with the first fluid. The fluid and the mixture are then sheared so that a plurality of monodispersed droplets is generated within the reaction tube. The monodisperse droplets generated comprise (i) at least a portion of the mixture, (ii) a single template particle providing to the droplet barcodes unique to the droplet, and (iii) a single cell. Of note, in practicing methods of the invention provided by this disclosure a substantial number of the monodispersed droplets generated will comprise a single template particle and a single cell, however, in some instances, a portion of the monodispersed droplets may comprise none or more than one template particle or cell. In such instances, monodispersed droplets comprising no cells, greater than one cell, no template particles and/or or greater than one template particle (are therefore greater than one barcode) may be excluded from further analysis.

Figure 1:
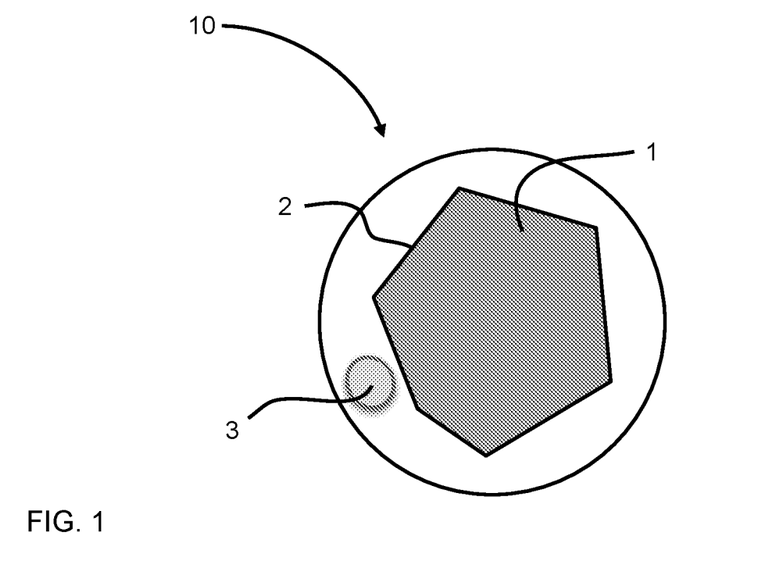
FIG. 1 shows a monodispersed droplet according to one aspect of the invention.
Figure 2:
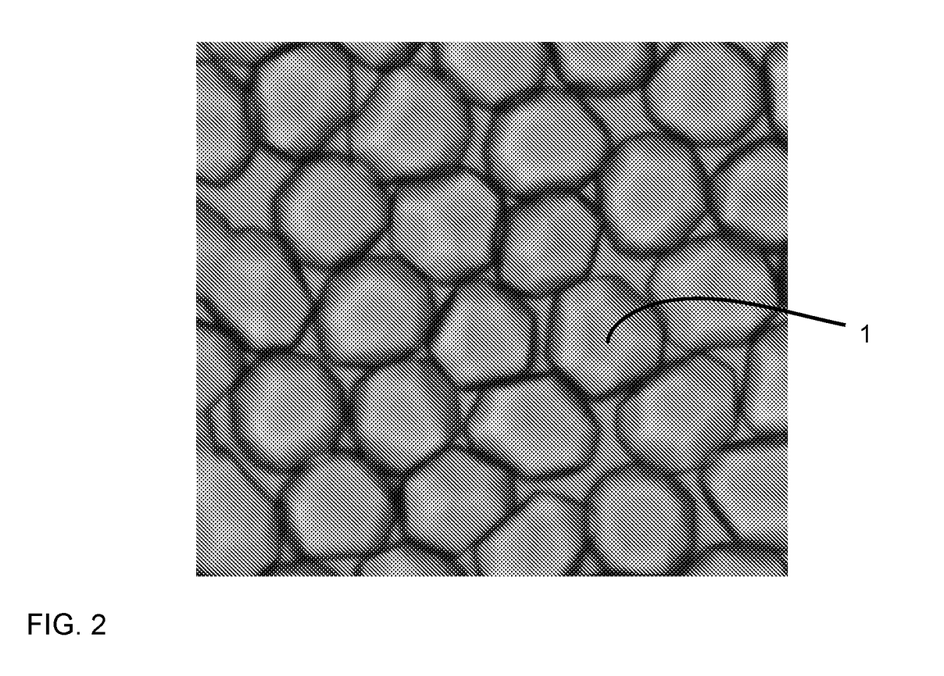
FIG. 2 shows a micrograph of a monodispersed droplet containing a flat faceted template particle according to an embodiment of FIG. 1.

FIG. 1 shows a monodispersed droplet according to one aspect of the invention. The depicted monodispersed droplet 10 comprises a template particle 1, a single cell 3. The template particle illustrated comprises flat facets 2, and provides unique barcode molecules to the droplet. FIG. 2 shows a micrograph of flat faceted template particles 1 according to an embodiment of FIG. 1. Each monodispersed droplet 1 in FIG. 2 contains unique barcodes, distinguishable from the barcodes used by any other droplet. In some embodiments, the first fluid is an aqueous phase fluid and the second fluid is an oil, e.g. fluorocarbon oil, a silicone oil, or a hydrocarbon oil, or a combination thereof.

To increase the chances of generating an encapsulation, such as, a monodispersed droplet 10 that contains one template particle 1 and one single cell 3, the template particles and cells may be combined at a ratio wherein there are more template particles than cells. For example, the ratio of template particles to cells combined in a mixture as described above may be in a range of 5:1 to 1,000:1, respectively. The template particles and cells may also be combined at a ratio of 10:1, 100:1, or 1000:1, respectively.

To generate a monodisperse emulsion 10, a step of shearing the second mixture provided by combining a first mixture comprising template particles and cells with a second fluid immiscible with the first mixture. Any suitable method may apply a sufficient shear force to the second mixture. For example, the second mixture may be sheared by flowing the second mixture through a pipette tip. Other methods include, but are not limited to, shaking the second mixture with a homogenizer (e.g., vortexer), or shaking the second mixture with a bead beater. Vortexing may be performed for example for 30 seconds, or in the range of 30 seconds to 5 minutes. The application of a sufficient shear force breaks the second mixture into monodisperse droplets that encapsulate one of a plurality of template particles.

Generating the template particles-based monodisperse droplets may involve shearing two liquid phases. For example, the mixture may be the aqueous phase and comprise reagents selected from, for example, buffers, salts, lytic enzymes (e.g. proteinase k) and/or other lytic reagents (e. g. Triton X-100, Tween-20, IGEPAL, bm 135, or combinations thereof), nucleic acid synthesis reagents e.g. nucleic acid amplification reagents, or combinations thereof. The fluid may be the continuous phase and may be an immiscible oil such as fluorocarbon oil, a silicone oil, or a hydrocarbon oil, or a combination thereof. The fluid may advantageously comprise reagents such as surfactants (e.g. octylphenol ethoxylate and/or octylphenoxypolyethoxyethanol), reducing agents (e.g. DTT, beta mercaptoethanol, or combinations thereof).

In practicing methods as described herein, the composition and nature of the monodisperse droplets, e.g., single-emulsion and multiple-emulsion droplets, may vary. Advantageously, a surfactant may be used to stabilize the droplets 10. The monodisperse droplets described herein may be prepared as emulsions, e.g., as an aqueous phase fluid dispersed in an immiscible phase carrier fluid (e.g., a fluorocarbon oil, silicone oil, or a hydrocarbon oil) or vice versa. Accordingly, a droplet may involve a surfactant stabilized emulsion, e.g., a surfactant stabilized single emulsion or a surfactant stabilized double emulsion. Any convenient surfactant that allows for the desired reactions to be performed in the droplets may be used. In other aspects, monodisperse droplets are not stabilized by surfactants.

Figure 3:
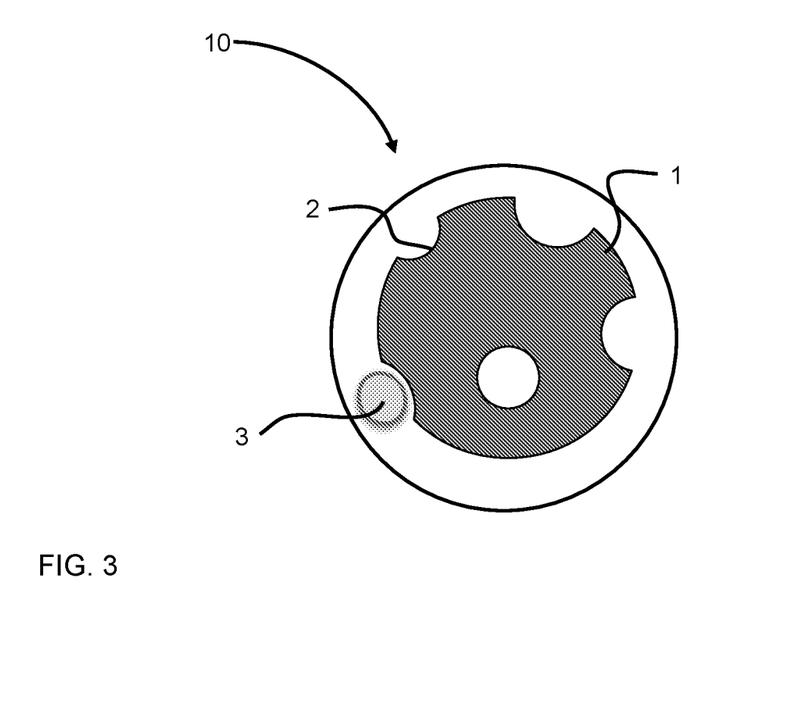
FIG. 3 shows a schematic representation of a monodispersed droplet containing an internal compartment.

FIG. 3 is a schematic representation of a single monodispersed droplet according to another embodiment of the present invention. The depicted monodispersed droplet 10 comprises a template particle 1 and a single cell 3. The template particle 3 illustrated comprises crater-like depressions 2, and, in the embodiment illustrated, the single cell 3 is associated with one of the crater-like depressions 2. The single cell 3 further comprises at least one internal compartment 4.

As described above, the template particles may contain multiple internal compartments 4. The internal compartments 4 of the template particles 1 may be used to encapsulate reagents that can be triggered to release a desired compound, e.g., a substrate for an enzymatic reaction, or induce a certain result, e.g. lysis of an associated single cell 3. Reagents encapsulated in the template particles' compartment 4 may be without limitation reagents selected from buffers, salts, lytic enzymes (e.g. proteinase k), other lytic reagents (e. g. Triton X-100, Tween-20, IGEPAL, bm 135), nucleic acid synthesis reagents, or combinations thereof.

The internal compartment 4 may also be used to encapsulate barcodes unique to template particle 1, and therefore to the droplet 10. When nucleic acid molecules are released from the cell 3, they are then tagged with the droplet specific barcode provided by the template particle 1. Once sequenced, each nucleic acid molecules can be identified with the source template particle 1, droplet 10, and cell 3.

Figure 4:
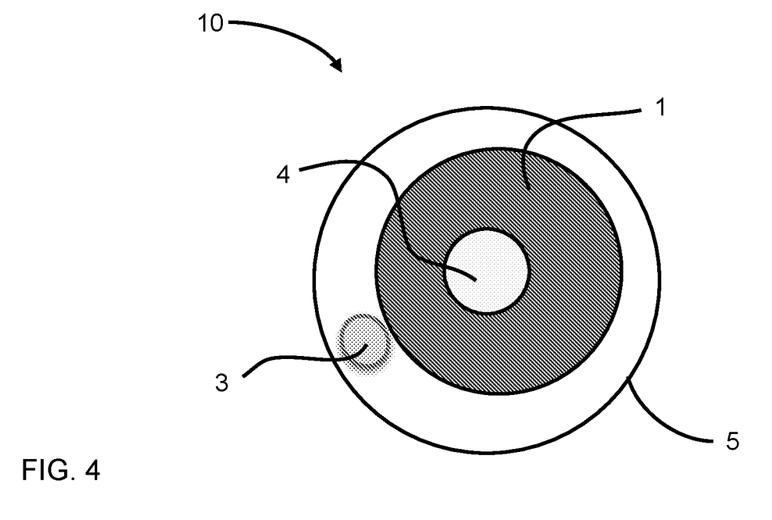
FIG. 4 shows a schematic representation of a monodispersed droplet containing an internal compartment.

FIG. 4 shows a schematic representation of another embodiment of one of a plurality of monodispersed droplets 10. The depicted monodispersed droplet 10 in FIG. 4 comprises a template particle 1 and a single cell 3. The template particle 1 illustrated is generally spherical, and in the embodiment illustrated, the single cell 3 is associated with the template particle 1. The template particle 1 further comprises an internal compartment 4, the internal compartment 4 comprises reagents, such as, for example, lytic reagents. The internal compartment 4 may also be used to encapsulate barcodes unique to template particle 1, and therefore to the droplet 10.

Figure 5:
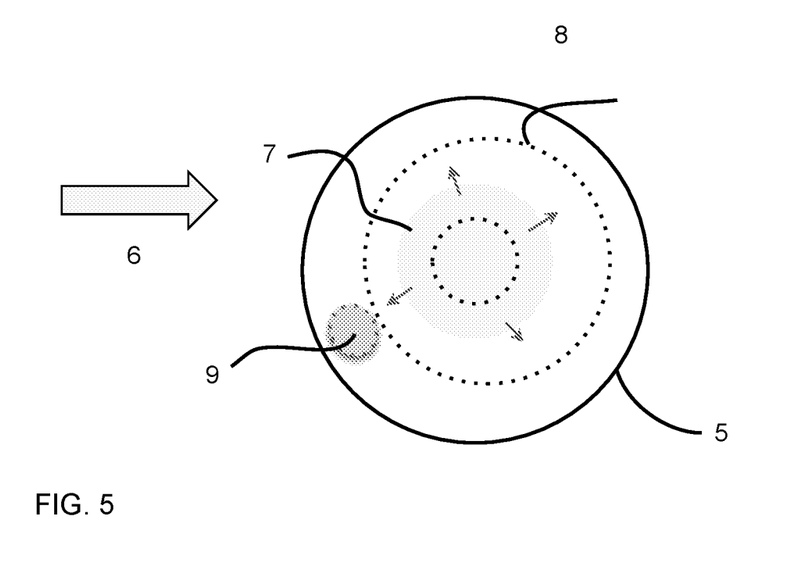
FIG. 5 shows a schematic representation of a monodispersed droplet after release of nucleic acid molecules from a single cell.

FIG. 5 shows a schematic representation of the monodispersed droplet following an external stimulus 6. After the external stimulus 6 is applied, lytic reagents are activated and released, dissolving 8 the template particle 1 and lysing the single cell 9, while the monodispersed droplet 10 remains intact as depicted by the intact encapsulation shell 5. In some embodiments, the external stimulus 6 may be heat or osmotic pressure. Within the droplet, each nucleic acid molecule is tagged with a barcode unique to the droplet, which remains intact to allow for each nucleic acid molecule to be tagged.

Releasing nucleic acid molecules from single cells may comprise lysis of the single cells within the monodispersed droplets 10. Lysis may be induced by a stimulus such as heat, osmotic pressure, lytic reagents (e.g., DTT, beta-mercaptoethanol), detergents (e.g., SDS, Triton X-100, Tween-20), enzymes (e.g., proteinase K), or combinations thereof. As depicted in FIG. 3, one or more of the said reagents (e.g., lytic reagents, detergents, enzymes) may be compartmentalized 4 within the template particle 1. In other embodiments, one or more of the said reagents is present in the mixture. In some other embodiments, one or more of the said reagents is added to the solution comprising the monodisperse droplets 10, as desired.

Methods of the invention generally relate to analysis and sequencing of barcoded nucleic acid molecules from single cells. Methods include releasing nucleic acid molecules from single cells 3 segregated inside monodispersed droplets 10, tagging each nucleic acid molecule with barcode unique to the monodispersed droplet, and then sequencing the nucleic acid molecule. Sequencing may analyze genomic areas of interest, e.g. oncogenes. Thus, PCR amplification of products derived from nucleic acid molecules released by single cells can be used to determine a cell genotype for preselected gene mutations, e.g., mutations associated with cancer. Genes and mutations of interest may include, but are not limited to, BAX, BCL2L1, CASP8, CDK4, ELK1, ETS1, HGF, JAK2, JUNB, JUND, KIT, KITLG, MCL1, MET, MOS, MYB, NFKBIA, EGFR, Myc, EpCAM, NRAS, PIK3CA, PML, PRKCA, RAF1, RARA, REL, ROS1, RUNX1, SRC, STAT3, CD45, cytokeratins, CEA, CD133, HER2, CD44, CD49f, CD146, MUC1/2, ABL1, AKT1, APC, ATM, BRAF, CDH1, CDKN2A, CTNNB1, EGFR, ERBB2, ERBB4, EZH2, FBXW7, FGFR2, FGFR3, FLT3, GNAS, GNAQ, GNAll, HNF1A, HRAS, IDHL IDH2, JAK2, JAK3, KDR, KIT, KRAS, MET, MLH1, NOTCH1, NPM1, NRAS, PDGFRA, PIK3CA, PTEN, PTPN11, RB1, RET, SMAD4, STK11, TP53, VHL, and ZHX2. For example, identification of a gene or mutation of interest may provide information that the cell from which the nucleic acid molecule was released has a cancer genotype or is a cancer cell. Because each nucleic acid molecule is tagged with a barcode unique to the droplet and single cell from which it was released, any gene or mutation of interest may be traced back to the droplet and single cell, thereby allowing for the identification of a cancer genotype in the cell. For RNA or mRNA sequencing, sequencing may first comprise the step of preparing a cDNA library from barcoded RNA, through reverse transcription, and sequencing the cDNA. RNA sequencing may advantageously allow for the quantification of gene expression within the single cell, and can be used to identify characteristics of the single cell that can be used to, for example, make a diagnosis, prognosis, or determine drug effectiveness. Reverse transcription of cDNA molecules from RNA can be performed both within the droplet or after barcoded RNA molecules have been released from each droplet.

Reverse transcription may be performed using without limitation dNTPs (mix of the nucleotides dATP, dCTP, dGTP and dTTP), buffer/s, detergent/s, or solvent/s, as required, and suitable enzyme such as polymerase or reverse transcriptase. The polymerase used may be a DNA polymerase, and may be selected from Taq DNA polymerase, Phusion polymerase (as provided by Thermo Fisher Scientific, Waltham, Mass.), or Q5 polymerase. Nucleic acid amplification reagents are commercially available, and may be purchased from, for example, New England Biolabs, Ipswich, Mass., USA. The reverse transcriptase used in the presently disclosed targeted library preparation method may be for example, maxima reverse transcriptase. In some embodiments, the general parameters of the reverse transcription reaction comprise an incubation of about 15 minutes at 25 degrees and a subsequent incubation of about 90 minutes at 52 degrees.

Sequencing nucleic acid molecules may be performed by methods known in the art. For example, see, generally, Quail, et al., 2012, A tale of three next generation sequencing platforms: comparison of Ion Torrent, Pacific Biosciences and Illumina MiSeq sequencers, BMC Genomics 13:341. Nucleic acid molecule sequencing techniques include classic dideoxy sequencing reactions (Sanger method) using labeled terminators or primers and gel separation in slab or capillary, or preferably, next generation sequencing methods. For example, sequencing may be performed according to technologies described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232, 656, 7,598,035, 6,306,597, 6,210,891, 6,828,100, 6,833,246, and 6,911,345, each incorporated by reference.

The conventional pipeline for processing sequencing data includes generating FASTQ-format files that contain reads sequenced from a next generation sequencing platform, aligning these reads to an annotated reference genome, and quantifying expression of genes. These steps are routinely performed using known computer algorithms, which a person skilled in the art will recognize can be used for executing steps of the present invention. For example, see Kukurba, Cold Spring Harb Protoc, 2015 (11):951-969, incorporated by reference.

The invention provides for a method for identifying a rare cell, such a cancer cell during early cancer detection, from a heterogeneous cell population. The method includes isolating a plurality of single cells from the heterogeneous cell population by combining the heterogeneous cells with a plurality of template particles in a first fluid, adding a second fluid that is immiscible with the first fluid, and shearing the fluids to generate an emulsion comprising monodispersed droplets that each contain a single cell and a single template particle. Methods further include releasing nucleic acid molecules from each of the single cells within the monodispersed droplets, tagging each nucleic acid molecule with a barcode unique to the monodispersed droplet, and sequencing the nucleic acid molecule. The method allows for the detection of cancer cells in both low and high volumes of sample, wherein each cell is simultaneously separated and the nucleic acid molecule tagged to single cell from which the nucleic acid molecule was released, however rare the single cell is within the sample.

For example, the method allows for analysis of a heterogeneous tumor biopsy taken from a subject. The method includes obtaining a biopsy from a patient and isolating a population of cells from the biopsy. The method further includes segregating the population of cells taken from the biopsy into droplets by combining the population of cells with a plurality of template particles in a first fluid, adding a second fluid that is immiscible with the first fluid, and shearing the fluids to generate an emulsion comprising monodispersed droplets that each contain a single one of the population of cells and a single template particle. Methods further include releasing nucleic acid molecules from each one of the segregated single cells contained within the monodispersed droplets, tagging each nucleic acid molecule with a barcode unique to the droplet, and sequencing the nucleic acid molecule to identify one or more genotypic characteristics of a tumor. Advantageously, the unique barcode is provided to the droplet by the template particle. The method disclosed can further comprise the step of using a genotype to diagnose a subject with cancer or a cancer stage or to devise a treatment plan, for example based on the number of cells identified as a cancer cell.

Nucleic Acid molecules may advantageously be amplified prior to sequencing. Amplification may comprise methods for creating copies of nucleic acids by using thermal cycling to expose reactants to repeated cycles of heating and cooling, and to permit different temperature-dependent reactions (e.g. by Polymerase chain reaction (PCR). Any suitable PCR method known in the art may be used in connection with the presently described methods. Non limiting examples of PCR reactions include real-time PCR, nested PCR, multiplex PCR, quantitative PCR or touchdown PCR. Notably, each amplified copy of the nucleic acid molecule will comprise the barcode unique to a droplet for identifying the droplet and cell form which the nucleic acid molecule was released.

Template particles may also comprise a plurality of capture probes. Generally, a capture probe is an oligonucleotide. The capture probes may attach to the template particle's material via covalent acrylic linkages. The capture probes may comprise an acrydite-modified on their 5' end (linker region). Generally, acrydite-modified oligonucleotides can be incorporated, stoichiometrically, into hydrogels such as polyacrylamide, using standard free radical polymerization chemistry, where the double bond in the acrydite group reacts with other activated double bond containing compounds such as acrylamide. Specifically, copolymerization of the acrydite-modified capture probes with acrylamide including a crosslinker, e.g. N,N'-Methylenebis, will result in a crosslinked gel material comprising covalently attached capture probes. Capture probes may also comprise Acrylate terminated hydrocarbon linker and combining the said capture probes with a template particle will cause their attachment to the template particle.

The capture probe may comprise one or more of a primer sequence, the barcode unique to each droplet, a unique molecule identifier (UMI), and/or a capture sequence.

Primer sequences may comprise a binding site, for example a primer sequence that would be expected to hybridize to a complementary sequence, if present, on any nucleic acid molecule released from a cell and provide an initiation site for a reaction, for example an elongation or polymerization reaction. The primer sequence may also be a "universal" primer sequence, i.e. a sequence that is complimentary to nucleotide sequences that are very common for a particular set of nucleic acid fragments. The primer sequences used may be P5 and P7 primers as provided by Illumin, Inc., San Diego, Calif. The primer sequence may also allow the capture probe to bind to a solid support, such as a template particle.

By providing capture probes comprising the barcode unique to each droplet, the capture probes may be use to tag the nucleic molecules released from single cells with the barcode. This process, discussed further herein below, may comprise hybridizing the nucleic acid molecule to the capture probe followed by an amplification or reverse transcription reaction.

Unique molecule identifiers (UMIs) are a type of barcode that may be provided to nucleic acid molecules in a sample to make each nucleic acid molecule, together with its barcode, unique, or nearly unique. This is accomplished by adding, e.g. by ligation, one or more UMIs to the end or ends of each nucleic acid molecule such that it is unlikely that any two previously identical nucleic acid molecules, together with their UMIs, have the same sequence. By selecting an appropriate number of UMIs, every nucleic acid molecule in the sample, together with its UMI, will be unique or nearly unique. One strategy for doing so is to provide to a sample of nucleic acid molecules a number of UMIs in excess of the number of starting nucleic acid molecules in the sample. By doing so, each starting nucleic molecule will be provided with different UMIs, therefore making each molecule together with its UMIs unique. However, the number of UMIs provided may be as few as the number of identical nucleic acid molecules in the original sample. For example, where no more than six nucleic acid molecules in a sample are likely to be identical, as few as six different UMIs may be provided, regardless of the number of starting nucleic acid molecules.

UMIs are advantageous in that they can be used to correct for errors created during amplification, such as amplification bias or incorrect base pairing during amplification. For example, when using UMIs, because every nucleic acid molecule in a sample together with its UMI or UMIs is unique or nearly unique, after amplification and sequencing, molecules with identical sequences may be considered to refer to the same starting nucleic acid molecule, thereby reducing amplification bias. Methods for error correction using UMIs are described in Karlsson et al., 2016, Counting Molecules in cell-free DNA and single cells RNA", Karolinska Institutet, Stockholm Sweden, available at <https://openarchive.ki.se/xmlui/handle/10616/45053>, incorporated herein by reference.

Capture sequences used in capture probes are advantageous for targeting gene-specific nucleotide sequences, for example nucleotide sequences known to be associated with a particular cancer genotype or phenotype. In such methods, the target nucleic sequence, if present, attaches to the template particle by hybridizing to the capture sequence upon release from the single cells.

Figure 6:
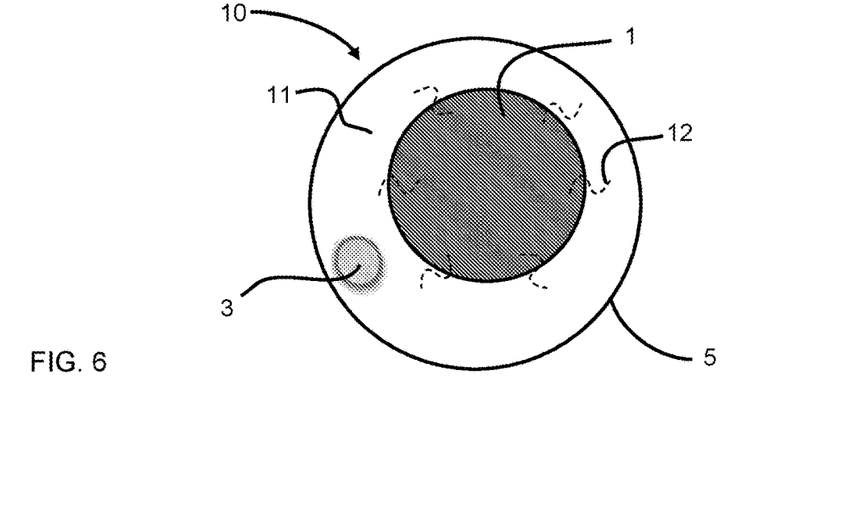
FIG. 6 shows a schematic representation of a method for single cell analysis according to some aspects of the present disclosure.

FIG. 6 show a schematic representation of monodispersed droplet. The depicted monodispersed droplet 10 comprises a template particle 1 and a single cell 3. The template particle 1 illustrated is generally spherical and comprises multiple capture probes 12, which may advantageously comprise the barcode unique to the droplet. Reagents, such as lytic reagents 11, are present within the monodispersed droplet 10.

Figure 7:
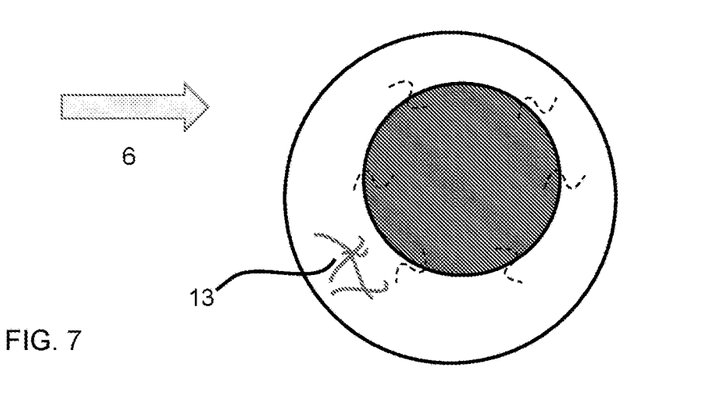
FIG. 7 shows a schematic representation of a monodispersed droplet after release of nucleic acid molecules from a single cell.
Figure 8:
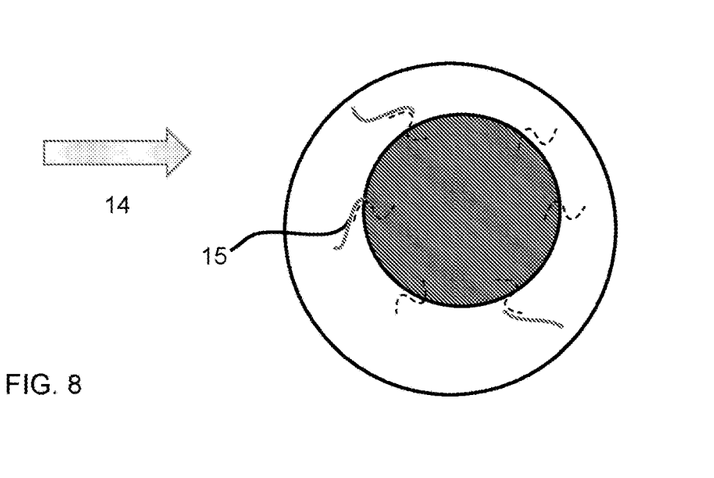
FIG. 8 shows a schematic representation of a monodispersed droplet with capture probes.

FIG. 7 shows the monodispersed droplet of FIG. 6 following an external stimulus 6. Following the stimulus 6 lytic reagents 11 are activated, lysing the single cell 3, while the encapsulation, i.e., monodispersed droplet 10 (depicted intact encapsulation shell 5) and template particle 1 remain intact. Upon lysis of the single cell 3, nucleic acid molecules 15 previously contained in the cell are released into the monodispersed droplet 10. A portion of the released nucleic acid molecules 15 associates with a portion of the capture probes 12 as depicted in FIG. 8. Advantageously, the capture probe may comprise the barcode unique to the monodispersed droplet and may be used to tag the nucleic acid molecule with the barcode.

Nucleic acid molecules hybridized to capture probes may be released for example by dissolving the template particle or by using a reducing reagent to reduce the dithiol oligonucleotide modifications in a capture probe linker region. Steps subsequent to the association of nucleic acid molecules and capture probes, such as amplification, may be done either inside the encapsulations or in bulk. When performing steps in bulk, an aqueous solution comprising the medium inside the encapsulations is generated upon breakage of the encapsulations. Any reagents, such as lytic reagents or nucleic acid synthesis reagents may be supplied in bulk, provided upon creation of the partitions (e.g., present in the first mixture), compartmentalized within the template particles, or combinations thereof.

Figure 9:
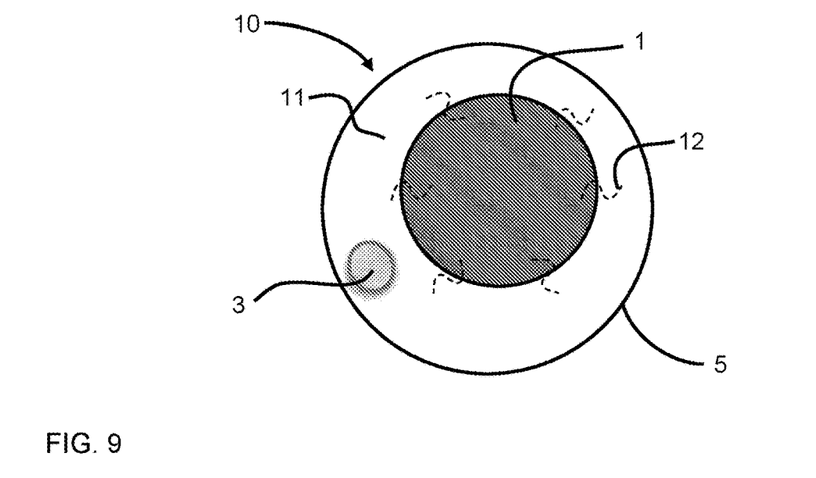
FIG. 9 diagrams a method for single cell analysis according to other aspects of the present disclosure.

FIG. 9 shows a schematic representation a method for single cell analysis according to other aspects of the present disclosure. Depicted is a single monodispersed droplet 10 from among a plurality of monodispersed droplets, which comprises a template particle 3 and a target cell 1. The template particle 1 comprises multiple capture probes 12. As described above, the each capture probe may comprise the barcode unique to the droplet. Reagents, such as lytic reagents 11, are present within the monodispersed droplet 10.

Figure 10:
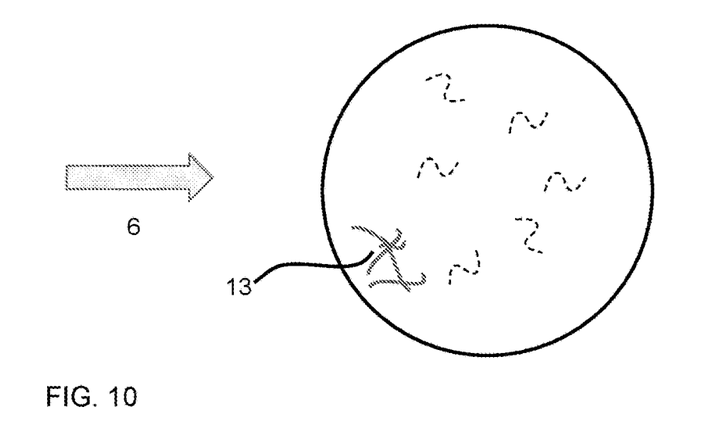
FIG. 10 shows a schematic representation of a monodispersed droplet after release of nucleic acid molecules from a single cell and dissolution of the template particle.
Figure 11:
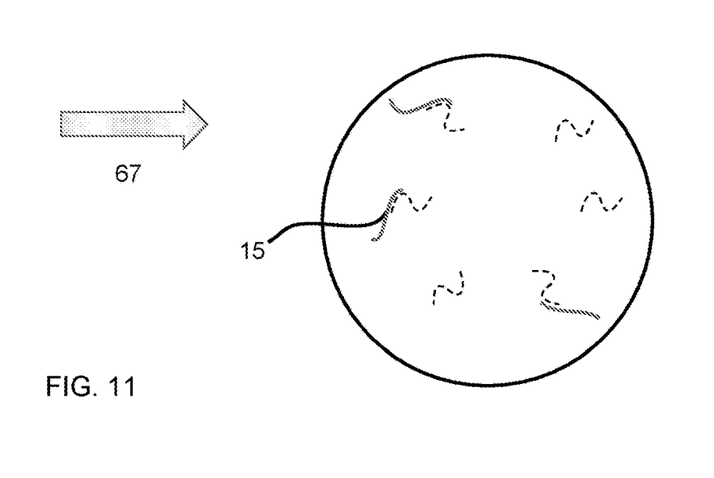
FIG. 11 shows a schematic representation of a monodispersed droplet with capture probes.

FIG. 10 shows the monodispersed droplet of FIG. 9 following an external stimulus 6. Following an external stimulus 6 the lytic reagents 11 are activated, lysing the single cell 3 and dissolving the template particle 1, however the monodispersed droplet 10 remains intact (depicted is the encapsulation shell 5). As the template particle 1 dissolves the capture probes 12 are released from it. Upon lysis of the single cell 3, nucleic acid molecules 15 previously contained in the single cell 3 are released. A portion of the released nucleic acid molecules 15 associates with the capture probes 12, as depicted in FIG. 11. Even without the template particle present, the capture probe may comprise the barcode unique to the monodispersed droplet and may be used to tag the nucleic acid molecule with the barcode.

Figures 12, 13:
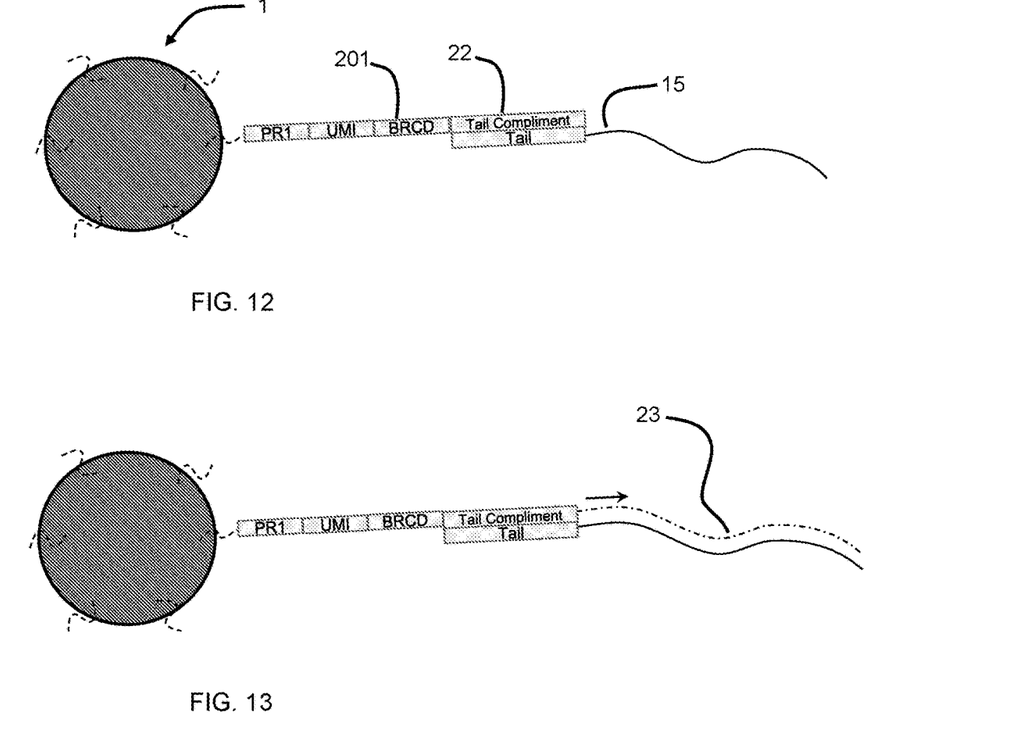
FIG. 12 shows a representation of a capture probe.
FIG. 13 shows a representation of first complimentary strand synthesis.

FIG. 12 shows a method of barcoding a nucleic acid with a capture probes according to certain aspects of the present disclosure. As illustrated, the template particle 1 comprises a plurality of capture probes 12 illustrated schematically by curved broken lines. One of the capture probes 12 is featured in a larger scale and in detail. The capture probe 12 preferably comprises, from 5' end to 3' end, a linker region to allow covalent bond with the template particle 1, a "PR1" nucleotide sequence region comprising a primer nucleotide sequence, at least one UMI, a barcode unique to the droplet 201 ("BRCD"), and a capture nucleotide sequence 22 comprising a sequence complimentary to the nucleic acid molecule.

FIG. 13 shows a released nucleic acid molecule 15 comprising, optionally, a tail sequence. The nucleic acid molecule attaches to the capture probe of FIG. 12's complimentary sequence 22 via complementary base pairing. For RNA molecules, the poly-A tail of an RNA molecule may be used to attach the RNA molecule to the capture probe, for example by using a capture prove with a poly-T sequence. Following the hybridization of the nucleic acid molecule 15 and the capture probe 12, a polymerase (or a reverse transcriptase in the case of RNA) is used to generate a first complimentary strand 23. For analysis of RNA, the first complimentary strand may be a cDNA strand. The first strand 23 comprises a compliment to nucleic acid molecule and the barcode sequence 201. The nucleic acid molecule 15—first complimentary strand 23 hybrid may be denatured (not shown) using any method traditional in the art, such as an exposure to a denaturing temperature.

Figure 14:
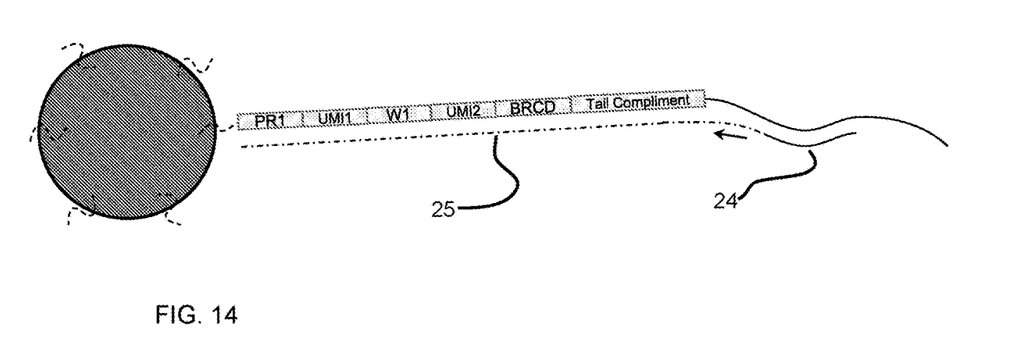
FIG. 14 shows a representation of second complimentary strand synthesis

FIG. 14 shows the complex of FIG. 13, in which a second strand primer 24 comprising a random hexamer sequence anneals with the first strand 23 to form a DNA-primer hybrid. A DNA polymerase is used to synthesize a second complementary strand 25 complimentary to the first strand. The second complimentary strand comprises the sequence of the released nucleic acid molecule and the barcode unique to the droplet. Upon being denatured from the first complimentary strand, the second complimentary strand may be sequenced and the sequence of the barcode may be used to identify the droplet and cell from which the nucleic acid molecule was released.

Methods employing one or more of ligation tagging and capture probe tagging of nucleic acid molecules with droplet specific barcodes and/or UMIs may be performed.

The complement of a nucleic acid when aligned need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

Figure 15:
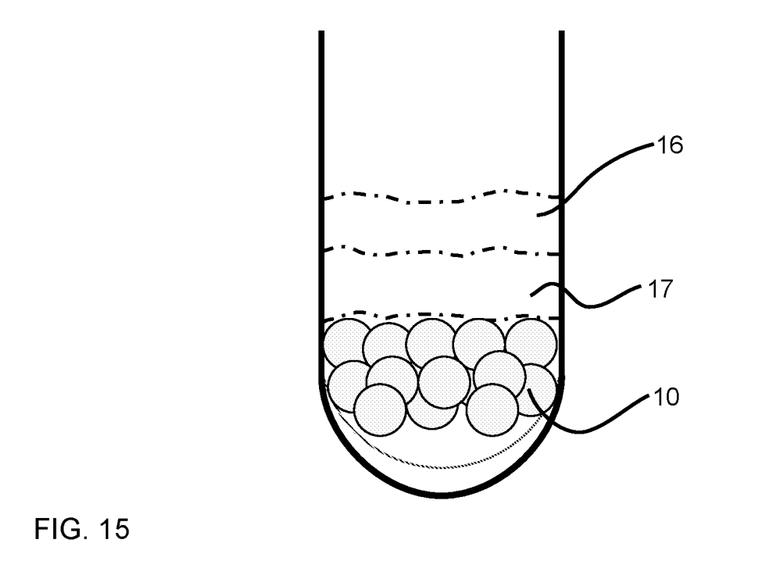
FIG. 15 shows a schematic representation of monodispersed droplets in a tube.
Figure 16:
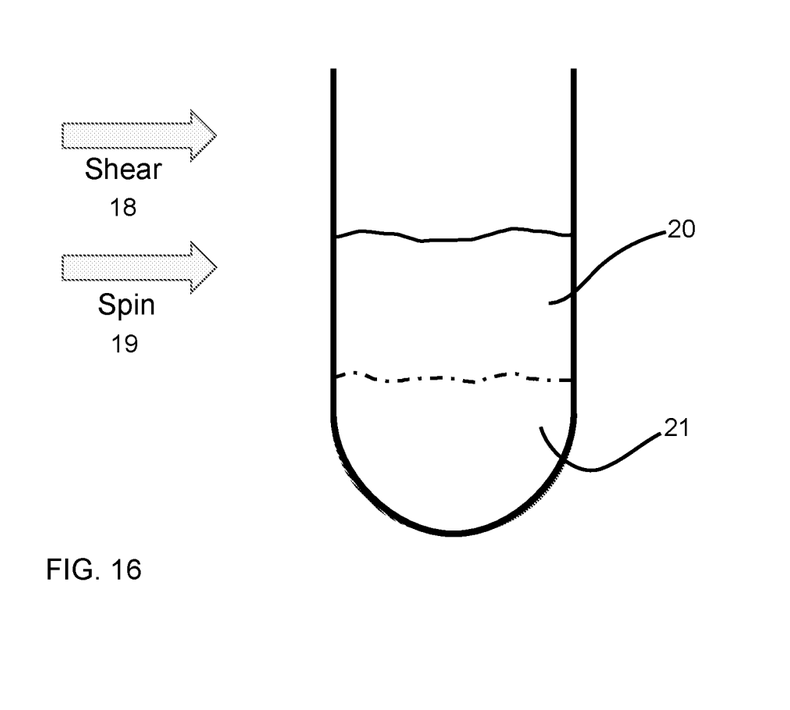
FIG. 16 shows a schematic representation of a method for rupturing monodispersed droplets.

FIG. 15 and FIG. 16 show a schematic representation of a method for rupturing the monodispersed droplets 10 according to aspects of this disclosure. The monodispersed droplets 10 are depicted as circles present in a fluid in the bottom portion of a test tube. The fluid comprising the encapsulations is topped with reagents such a high salt buffer (middle layer), and breaker reagent (top layer). The high salt buffer may comprise beta mercaptoethanol and/or DTT, or other reducing reagents. The breaker reagent may comprise perfluorooctanol (PFO). Incubation of the fluid with the high salt buffer and breaker reagent is preferably done on ice.

FIG. 16 shows the monodispersed droplets of FIG. 15 following the steps of mixing by, for example, vortex, shearing 18, and/or spin 19. The monodispersed droplets 10 are broken, and two layers 20, 21, aqueous and oil are formed. Depending on the type of oil used, the oil layer may be the bottom layer or the top layer. The template particles and any nucleic acids associated with them are present in the aqueous layer.

Nucleic acid molecules, including capture probe bound nucleic acid molecules, released nucleic acid molecules, or amplified nucleic acid molecules, may be attached to streptavidin-coated magnetic beads. For example, streptavidin-coated magnetic beads bound to biotin-labeled oligonucleotides comprising a bait sequence may be used. The bait sequence may be complementary to a primer sequence of the nucleic acid molecule, which may be for example, the one or more UMIs the droplet unique barcode on the released nucleic acid molecule. The streptavidin-coated magnetic beads comprising the bait sequence may then be incubated with the nucleic acid molecule to allow hybridization of complementary sequences. The nucleic acid molecule may first be incubated with biotin-labeled oligonucleotides comprising a bait sequence, wherein the bait sequence is complementary to one or more barcodes of the nucleic acid molecule to allow hybridization of complementary sequences. Following the incubation, streptavidin-coated magnetic beads are added and further incubated with the nucleic acid molecule/biotin-labeled oligonucleotide mixture to allow streptavidin-biotin binding. Incubation steps may be done on ice.

Alternatively, general nucleic acid capture beads may be used, for example polystyrene beads surrounded by a layer of magnetite and/or carboxyl molecules, such as beads with a similar surface characteristic to SPRI beads. SPRI beads may be as described in Deangelis et al. (1995) "Solid-phase reversible immobilization for the isolation of PCR products", Nucleic Acids Res. 23(22):4742-3, incorporated by reference.

Template particles used in the present invention may further comprise a capture moiety. The capture moiety acts to capture specific cells, for example, specific types of cells. The capture moiety may comprise an Acrylate-terminated hydrocarbon linker with biotin termination. The capture moiety may be attached to a target-specific capture element, for example aptamers and/or antibodies. Examples of capture moieties and methods thereof are disclosed in PCT application no. PCT/US2019/053426, incorporated herein by reference.

As described above, tubes may be selected based on the volume of sample from which cells need to be separated and/or based on the number of cells to be separated. For example, the tube may be single large tube, such as a conical centrifuge tube, such as a Falcon® as sold by Corning Inc., Corning, N.Y., for example a tube with a volume of less than 40 mL. Such tubes may be advantageous where the number of cells to be analyzed is between 100,000 and 1 million cells or greater than 1 million cells. This method is useful when analyzing cells for targeted coverage of heterogeneous cell types and exploring pathways in complex tissues, for example in cancer detection in mixed cell populations.

The tubes may also be wells, such as standard 96 sample well kit. The well may be part of a microplate with multiple wells each used a tube. The microplate may comprise any number of wells as desired, for example 6-1536 wells. Advantageously, the microplate may comprise 96 wells. Wells may be advantageous where the number of cells to be analyzed is about 100 cells. This method is useful when deep profiling homogenous cells under different conditions, such as early cancer detection in a tumor site.

The tubes may also be centrifuge, microcentrifuge, or PCR tubes, such as those sold be Eppendorf®, Hamburg, Germany. Such tubes, for example, may be between 0.1 and 6 mL and are advantageous where the number of cells to be analyzed is about 10,000 cells. This method is useful when deep profiling heterogeneous cell populations, for example in early cancer detection in mixed cell populations.

As described above, because cells are encapsulated in mono-dispersed droplets simultaneously, methods of the present invention are easily scaled for the analysis of any number of cells. For example, tubes may be selected to analyze at least 1 million cells, at least 2 million cells, at least 10 million, at least than 100 million cells, or 200 million cells of greater. Additionally, because cells are encapsulated simultaneously, for any tubes and any number of cells sample preparation for sequencing may be completed within one day, and can be completed within three hours. Moreover, preparation of samples within each tube may be completed in as little time as about 5 minutes or about 2 minutes.

Primers and/or reagents may be added to the monodisperse droplets after formation of the monodisperse droplets in the tube. Primers and/or reagents may be added in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, PCR primers may be added in a separate step from the addition of a lysing agent.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for single cell analysis, the method comprising:
combining a plurality of template particles, each comprising a unique barcode, and single cells;
generating a plurality of monodispersed droplets simultaneously that encapsulate a single template particle and a single cell;
releasing nucleic acid molecules from the single cells; and
analyzing the nucleic acid molecules.

2. The method of claim 1, wherein the nucleic acid molecules are DNA or RNA molecules.

3. The method of claim 1, wherein the template particles comprise one selected from the group consisting of agarose, alginate, polyethylene glycol, polyacrylamide, acrylate, acrylamide, and bis-acrylamide.

4. The method of claim 1, wherein the template particles are spherical.

5. The method of claim 1, wherein the monodisperse droplets are deposited in a tube.

6. The method of claim 1, wherein the template particles are dehydrated prior to said combining step.

7. The method of claim 1, wherein said single cells are obtained from a tissue or body fluid sample.

8. The method of claim 7, wherein the number of cells to be analyzed is 100,000 cells.

9. The method of claim 1, further comprising associating the nucleic acid molecules with cells from which they were obtained.

10. The method of claim 1, further comprising analyzing said nucleic acids for identification of a mutation.

11. The method of claim 10, wherein the mutation constitutes a cancer genotype.

12. The method of claim 11, further comprising staging cancer based on said genotype.

13. The method of claim 11, further comprising prescribing a treatment protocol.

14. The method of claim 1, wherein said analyzing step comprises PCR.

15. The method of claim 1, wherein the template particles are faceted.

16. The method of claim 1, wherein the template particles comprise internal compartments.

17. The method of claim 16, wherein the template particles are capable of triggered release of reagents from said internal compartments.

18. The method of claim 3, wherein said RNA is an mRNA.

* * * * *